(12) United States Patent
Samuels et al.

(10) Patent No.: US 8,980,910 B2
(45) Date of Patent: Mar. 17, 2015

(54) TREATMENT OF GLAUCOMA

(75) Inventors: Brian C. Samuels, Indianapolis, IN (US); Anantha Shekhar, Indianapolis, IN (US); Philip L. Johnson, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/009,294

(22) PCT Filed: Mar. 29, 2012

(86) PCT No.: PCT/US2012/031160
§ 371 (c)(1),
(2), (4) Date: Oct. 1, 2013

(87) PCT Pub. No.: WO2012/135465
PCT Pub. Date: Oct. 4, 2012

(65) Prior Publication Data
US 2014/0039003 A1    Feb. 6, 2014

Related U.S. Application Data (60) Provisional application No. 61/470,850, filed on Apr. 1, 2011.

(51) Int. Cl.
| | | |
|---|---|---|
| *A01N 43/42* | (2006.01) | |
| *A61K 31/44* | (2006.01) | |
| *A61K 31/4375* | (2006.01) | |
| *A61K 31/472* | (2006.01) | |
| *A61K 31/551* | (2006.01) | |

(52) U.S. Cl.
CPC ........... *A61K 31/4375* (2013.01); *A61K 31/472* (2013.01); *A61K 31/551* (2013.01)
USPC ........................................................ 514/300

(58) Field of Classification Search
None
See application file for complete search history.

(56) References Cited

U.S. PATENT DOCUMENTS

2009/0192188 A1*    7/2009    Liu ............................... 514/307

OTHER PUBLICATIONS

Glaucoma Fact Sheet, Glaucoma Research Foundation, Apr. 22, 2013.*
Dias et al. (J Physiol, Mar. 9, 2009, 587.9, 2059-2067).*
Baxter et al. (Org. Process Res. Dev., Mar. 4, 2011, 15, 367-375).*
Wilensky, J.T., Diurnal Variations In Intraocular Pressure, TR. AM. Opth. Soc., vol. LXXXIX, 1991.
Liu et al., Variations in ocular hemodynamics in patients with early and late glaucoma, Acta Ophthalmologica Scandinavica, 1999.
Liu et al., Twenty-four-hour intraocular pressure pattern associated with early glaucomatous changes, Invest Ophthalmol Vi.s Sci., Apr. 2003; 44(4): pp. 1586-1590.
Asrani et al., Large diurnal fluctuations in intraocular pressure are an independent risk factor in patients with glaucoma, Apr. 2000; 9(2): pp. 134-142.
Lee el al., Association between intraocular pressure variation and glaucoma progression: data from a United States chart review, Dec. 2007, 144(6): pp. 901-907, Epub.
Hong et al., Long-term intraocular pressure fluctuation and progressive visual field deterioration in patients with glaucoma and low intraocular pressures after a triple procedure, Arch Ophthalmol, Aug. 2007; 125(8): pp. 1010-1013.
Caprioli and Coleman, Intraocular pressure fluctuation a risk factor for visual field progression at low intraocular pressures in the advanced glaucoma intervention study, Ophthalmology, Jul. 2008; 115(7): pp. 1123-1129.e3., Epub.
Valderrama et al., Detection of Glaucoma by means of ANNs, vol. 1240, pp. 986-994, Biological and Artificial Computation, 2005.
Moore and Eichler, Loss of a circadian adrenal corticosterone rhythm following suprachiasmatic lesions in the rat; pp. 201-206, Brain Research, 1972.
Mouret et al., Suprachiasmatic nuclei lesions in the rat: alterations in sleep circadian rhythms, Electroencephalography Clin. Neurophysiol., Sep. 1978; 45(3): pp. 402-408.
Liu et al., Suprachiasmatic nucleus in the neural circuitry for the circadian elevation of intraocular pressure in rabbits, J. Ocul Pharmacol Ther 11(3); pp. 379-388, 1995.
Shekhar et al., Post-penetrating keratoplasty glaucoma, 1993.
Ter Horst et al., The projections of the dorsomedial hypothalamic nucleus in the rat., Brain Res Bull vol. 16, pp. 231-248, 1986.
Casicio et al., The suprachiasmatic nuclei stimulate evening ACTH secretion in the rat, Brain Research, 423, pp. 173-179, 1987.
Chou et al., Critical Role of Dosomedial Hypothalamic Nucleus in a Wide Range of Behavioral Circadian Rhythms, The Journal of Neuroscience, vol. 23(33), pp. 10691-10702, 2003.
De Novellis et al., Hypothalamic sites mediating cardiovascular effects of microinjected bicuculline and EAAs in rats, The American Physiological Society, pp. R131-R140, 1995.
Johnson et al., Panic-Prone State Induced in Rats with GABA Dysfunction in the Dorsomedial Hypothalamus Is Medicated by NMDA Receptors, The Journal of Neuroscience, vol. 26(26), pp. 7093-7104, 2006.
Johnson et al., Neural Pathways Underlying Lactate Induced Panic, Neuropsychopharmacology, vol. 33(9), pp. 2093-2107, 2008.
Johnson et al., A Key Role for Orexin In Panic Anxiety, Nat. Med., vol. 16(1), pp. 111-115, 2010.
Keim et al., The effects of GABAA receptor blockade in the dorsomedial hypothalamic nucleus on corticotrophin (ACTH) and corticosterone secretion in male rats, Brain Research 739, pp. 46-51, 1996.
Madden et al., Excitatory amino acid receptors in the dorsomedial hypothalamus mediate prostaglandin-evoked thermogenesis in brown adipose tissue, Am. J. Physiol Regul Interg Comp Physiol 286, pp. R320-R325, 2004.

(Continued)

*Primary Examiner* — Dennis Heyer
*Assistant Examiner* — Daniel M Podgorski
(74) *Attorney, Agent, or Firm* — Stinson Leonard Street LLP (57) ABSTRACT

A method is provided for treating patients suffering from elevated intraocular pressure or fluctuation in intraocular pressure, including for example glaucoma patients. The method comprises administering to the patient an inhibitor of orexin activity in an amount sufficient to reduce intraocular pressure or intraocular pressure fluctuation in one or both eyes of the patient.

12 Claims, 5 Drawing Sheets

(56) References Cited

OTHER PUBLICATIONS

Samuels et al., Tachycardia evoked by disinhibition of the dorsomedial hypothalamus in rats is mediated through medullary raphe, Journal of Physiology, vol. 538.3, pp. 941-946, 2002.

Shekhar et al., The Circumventricular organs Form a Potential Neural Pathway for Lactate Sensitivity: Implications for Panic Disorder, The Journal of Neuroscience, vol. 17(24), pp. 9726-9735, 1997.

Shekhar et al., Dorsomedial Hypothalamic GABA Dysfunction Produces Physiological Arousal Following Sodium Lactate Infusions, Pharmacology Biochemistry & Behavior, vol. 55, No. 2, pp. 249-256, 1996.

Shekhar et al, Angiotensin-II Is a Putative Neurotransmitter in Lactate-Induced Panic-Like Responses in Rats with Disruption of GABAergic Inhibition in the Dorsomedial Hypothalamus, The Journal of Neuroscience, vol. 26(36), pp. 9205-9215, 2006.

Stotz-Potter et al., Effect of microinjection of muscimol into the dorsomedical or paraventricular hypothalamic nucleus on air stress-induced neuroendocrine and cardiovascular changes in rats, Brain Research 742, pp. 219-224, 1996.

Zaretskaia et al., Role of the dorsomedial hypothalamus in thermogenesis and tachycardia caused by microinjection of prostaglandin E2 into the preoptic area in anesthetized rats, Neuroscience Letters 340, pp. 1-4, 2003.

Zaretsky et al., Microinjection of muscimol into raphe pallidus suppresses tachycardia associated with air stress in conscious rats, J. Physiol, vol. 546.1, pp. 243-250, 2003.

* cited by examiner a. I-AG infusions directed at orexin neurons in hypothalamus

FIG. 1A b. "anxiety" associated behavior c. increased core temperature

TREATMENT OF GLAUCOMA

CROSS REFERENCE TO RELATED APPLICATIONS

This application claims priority to International Application Number PCT/US2012/031160, filed on Mar. 29, 2012, and U.S. Provisional Patent Application No. 61/470,850, filed on Apr. 1, 2011, the disclosures of which are hereby expressly incorporated by reference in their entireties.

BACKGROUND

Glaucoma is one of the leading causes of blindness worldwide. However, a fundamental understanding is still lacking regarding the pathophysiologic mechanisms underlying the optic nerve damage that occurs at the level of the lamina cribrosa. Elevated intraocular pressure (IOP) is known to be the primary cause of glaucoma, but there has been a great deal of debate over the role of IOP fluctuation in the development and progression of the glaucomatous optic neuropathy.

There is ample evidence demonstrating circadian IOP fluctuations, with the peak pressure occurring in the morning upon awakening (Wilensky, 1991; Liu et al., 1999; and Liu et al., 2003). Recently, a variety of studies, including the Advanced Glaucoma Intervention Study (AGIS) have identified IOP fluctuation as an independent risk factor for progression of glaucoma (Asrani et al., 2000; Lee el al, 2007; Hong el al., 2007; and Caprioli and Coleman, 2008). Identifying the neurophysiologic basis of IOP fluctuation and its role in glaucoma progression could profoundly impact the way patients with glaucoma are treated.

IOP varies in a cyclical manner over a 24-hour period in humans (Wilensky, 1991; Liu et al., 1999; Liu et al., 2003), and this circadian variation is conserved in rodents (Valderrama et al., 2005). Applicants hypothesized that the suprachiasmatic nucleus (SCN), which receives direct projections from retinal ganglion cells, may serve as a central control mechanism for these fluctuations. Known as the body's "master time-clock", the SCN has a variety of functions in regulating circadian activities, including corticosteroid release (Moore and Eichler, 1972; and Cascio et al., 1987) and sleep (Mouret et al., 1978). The SCN also appears to play a role in IOP fluctuations as well. Liu and Shieh have shown that SCN lesions alter circadian fluctuations in IOP (Liu and Shieh, 1995), yet the downstream circuitry mediating this effect is unknown.

As disclosed herein orexin containing neurons located in the dorsomedial hypothalamus (DMH) and/or the perifornical hypothalamus (PeF) are believed to play a role in mediating these circadian fluctuations in IOP. Orexins (also called hypocretins) are neuropeptides first discovered in the late 1990's. There are two forms of orexins, orexin A and orexin B (also known as hypocretin 1 and hypocretin 2, respectively), that are exclusively produced in hypothalamic neurons in the perifornical region (PeF) and lateral hypothalamic area (LHA 1). Orexin A and orexin B were initially identified as endogenous ligands for two orphan G-protein-coupled receptors, now known as orexin receptor-1 (ORX 1) and orexin receptor-2 (ORX2). The amino acid identity between the full length human ORX 1 and ORX2 sequences is 64%. ORX 1 has greater affinity for orexin A than orexin B by 1 order of magnitude. In contrast, ORX2 has similar affinity for both orexin A and orexin B.

Orexins constitute a novel peptide family with no significant structural similarities to known families of regulatory peptides. Orexin A is a 33-amino acid peptide of 3562 Da with two sets of intrachain disulfide bonds. It has an N-terminal pyroglutamyl residue and C-terminal amidation. The primary structure of orexin A predicted from the eDNA sequences is completely conserved among several mammalian species (human, rat, mouse, cow, sheep, dog, and pig). On the other hand, rat orexin B is a 28-amino acid, C-terminally amidated linear peptide of 2937 Da that is 46% ($^{13}/_{28}$) identical in sequence to orexin A. The C-terminal half of orexin B is very similar to that of orexin A (73%; 11115), whereas the N-terminal half is variable. Orexin A and B are produced from a common precursor polypeptide, prepro-orexin.

Classically, the DMH has been recognized as a regulator of the behavioral and physiological responses to emotional stress that includes anxiety-associated behavior (Shekhar, 1993), tachycardia (DeNovellis et al., 1995; Samuels et al., 2002; and Zaretsky et al., 2003), thermogenesis (Zaretskaia et al., 2003; and Madden and Morrison, 2004), and activation of the hypothalamic-pituitary-adrenal axis (Keirn and Shekhar, 1996; Stotz-Potter et al., 1996). Recently, Dr. Anantha Shekhar's laboratory has shown that orexin containing neurons, which are concentrated in the region of the DMH and PeF, play a profound role in mediating the physiologic and behavioral responses to panic (Johnson et al., 2010). Further, Chou and colleagues determined that orexin neurons and other neurons in the DMH receive strong direct and indirect projections from the SCN, and similar to the SCN, lesions in the orexin region affects the circadian pattern of corticosteroid release, sleep, locomotor activity, and feeding (Chou et al., 2003). With a broad array of efferent projections to autonomic sympathetic relays (ter Horst and Luiten, 1986), the DMH and orexin containing neurons are ideally situated to modulate the fluctuations in IOP evoked by circadian activity of SCN neurons.

Consistent with these observations applicants have proposed that the circadian fluctuations in intraocular pressure (IOP) are regulated in part by orexin containing neurons located in the dorsomedial hypothalamus (DMH) and perifornical region (PeF). Furthermore, applicants anticipate that an orexin antagonist could be used to attenuate these fluctuations, making it the first oral medication developed for the chronic treatment of glaucoma.

As disclosed herein, a method is provided for treating glaucoma, comprising the step of administering an orexin inhibitor.

SUMMARY

As disclosed herein orexin neurons and other neurons in the region of the dorsomedial hypothalamus (DMH) receive strong direct and indirect projections from the suprachiasmatic nucleus (SCN). Furthermore, administration of an orexin antagonist to the DMH region can attenuate physiological responses resulting from stimulation of the DMH by SCN neurons as a result of circadian activation by the SCN. Accordingly, applicants anticipate that an orexin antagonist could be used to attenuate the circadian fluctuations in intraocular pressure (IOP) that are regulated in part by orexin containing neurons located in the dorsomedial hypothalamus (DMH) and perifornical (PeF) region. Furthermore, inhibiting fluctuations in intraocular pressure provides a novel approach for the treatment of glaucoma even in patients having IOP within normal ranges.

In accordance with one embodiment composition and methods are provided for treating glaucoma. In one embodiment a method of lowering IOP or maintaining IOP at target treatment levels (i.e., suppressing an increase in IOP when the sympathetic nervous system is activated each morning in a circadian manner) is provided as a method of treating glaucoma or other elevated IOP related conditions. The method comprises administering to a patient in need of such treatment, a composition comprising an inhibitor of orexin activity. In one embodiment a method of reducing IOP fluctuations in patients is provided as a means treating glaucoma and reducing damage to the optic nerve. The composition can be administered prophylactically (e.g., based on family history or detected physical changes associated with glaucoma) or can be administered after the onset of the excessive IOP, the documentation of excessive IOP fluctuations, or progression of glaucoma.

Inhibitors of orexin activity are known to those skilled in the art and include the use of interfering RNA, anti-sense nucleic acids and peptide or other small molecules. In one embodiment the inhibitor is an orexin 1 receptor (ORX1) antagonist/inhibitor. In another embodiment the antagonist/inhibitor is a selective for the orexin 2 receptor (ORX2). In a further embodiment the inhibitor is a dual orexin receptor antagonist (DORAs). In one embodiment the method comprises the administration of one or more orexin inhibitors selected from the group consisting of SB334867, MK4305 and Almorexant.

Accordingly, in one embodiment, the present disclosure is directed to a method of treating glaucoma in a patient in need thereof. The method comprises administering to the patient an effective amount of a composition comprising an inhibitor or orexin activity selected from the group consisting of an orexin antagonist, an antibody and a nucleic acid.

In another embodiment, the present disclosure is directed to a method of reducing intraocular pressure in a patient in need thereof. The method comprises administering to the patient an effective amount of a composition comprising an inhibitor or orexin activity selected from the group consisting of an orexin antagonist, an antibody and a nucleic acid.

In yet another embodiment, the present disclosure is directed to a method of maintaining intraocular pressure in a patient in need thereof. The method comprises administering to the patient an effective amount of a composition comprising an inhibitor or orexin activity selected from the group consisting of an orexin antagonist, an antibody and a nucleic acid.

BRIEF DESCRIPTION OF THE DRAWINGS

FIG. 1A-E. presents data from an experiment where a panic prone rat model system is used to test the ability of an orexin 1 receptor (ORX1) antagonist SB334867 to ameliorate the panic response. The rats were initially made panic prone by a chronic infusion of a GABA synthesis inhibitor: 1-allylglycine [(1-AG; directed at orexin neurons that are exclusive to the dorsomedial and lateral hypothalamus (DMH and LH) (Peyron et al., 1998): see orexin immunoreactive neurons in FIG. 1A]. The panic prone mice were then systemically injected with either the orexin 1 receptor (ORX1) antagonist [SB334867, 30 mg/kg i.p., Tocris Bioscience, Bristol, UK, in 0.2 ml/100 g volume DMSO, i.p.] or vehicle control, prior to an ordinarily mild interoceptive stressor (i.e., 15 min i.v. infusion of 0.5M sodium lactate challenge). Administration of the orexin 1 receptor (ORX1) antagonist attenuated "anxiety"-like responses [social interaction (SI) duration; n=14, 8, 11, 12, 6; treatment effect $F(4,36)=17.8$, $p=0.001$], see FIG. 1B; and lactate induced increases in core body temperature (FIG. 1C; n=6/group, treatment×time effect $F(1\ 4,98)=1.9$, $p<0.04$); heart rate (FIG. 1D; HR, n=6/group; treatment×time effect $F(1\ 4,98)=5.4$, $p<0.001$) and general locomotor activity (FIG. 1E; n=6/group; treatment×time effect $F(1\ 4,98)=1.8$, $p<0.05$), * indicate significant differences between Vehicle treated groups and SB33 treatment group using Fisher's LSD poshoc tests that are protected with an ANOVA at each time point with $p<0.05$. Mean values of baseline temperature, HR and activity were not significantly different.

DETAILED DESCRIPTION DEFINITIONS

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable.

As used herein, the term "treating" includes prophylaxis of the specific disorder or condition, or alleviation of the symptoms associated with a specific disorder or condition and/or preventing or eliminating said symptoms. For example treating glaucoma may include inhibiting fluctuations in intraocular pressure, lowering IOP, maintaining IOP at target treatment levels, or any combination thereof. As used herein target treatment levels of IOP include IOP values anywhere from 10-21 mm Hg.

As used herein the term "inhibitor of orexin activity" is intended to encompass any safe and effective compound or treatment that can be administered to a patient to inhibit orexin activity in vivo. Orexin activity includes binding of an orexin (i.e., orexin A or orexin B) to one of its corresponding G-protein coupled orexin receptors, ORX1 and ORX2 and activation of signal transduction pathways.

As used herein, the phrase "elevated intraocular pressure" relates to any situation in which the pressure inside one or both eyes is higher than the goal intraocular pressure set by one skilled in the art of treating such eye problems. Eye pressure is typically measured in millimeters of mercury (mm Hg). Normal human eye pressure ranges from 10-21 mm Hg. Eye pressure of greater than 21 mm Hg is considered elevated in humans; however, there are conditions such as "normal tension glaucoma" in which the phenotype of glaucoma which includes visual field loss and damage to the optic nerve occur at pressures below 21 mmHg.

As used herein, the term "glaucoma" refers to any condition of the eye that is associated with stereotypical glaucomatous optic nerve damage (e.g., acquired atrophy of the optic nerve and loss of retinal ganglion cells and their axons) and corresponding visual field loss with or without the presence of elevated intraocular pressure.

As used herein an "effective" amount or a "therapeutically effective amount" of an orexin inhibitor refers to a nontoxic but sufficient amount of an inhibitor to provide the desired effect. For example one desired effect would be preventing the onset, or reducing the severity, frequency or duration of increased intraocular pressure (IOP) events. The amount that is "effective" will vary from subject to subject, depending on the age and general condition of the individual, mode of administration, the extent of the disease process and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein the term "patient" without further designation is intended to encompass any warm blooded vertebrate domesticated animal (including for example, but not limited to livestock, horses, cats, dogs and other pets) and humans.

Embodiments Detailed Description

As disclosed herein a method is provided for lowering intraocular pressure and/or intraocular pressure fluctuations in a patient, said method comprising the step of administering to a patient a composition comprising an inhibitor of orexin activity. Studies have shown that reducing intraocular pressure reduces the incidence of damage to the optic nerve. In particular individuals having intraocular pressures of greater than 21 mm Hg, have an average estimated risk of 10% of developing glaucoma over 5 years. This risk may be decreased to 5% (a 50% decrease in risk) if eye pressure is lowered by medications. Furthermore, for patients at risk of developing glaucoma, even those having intraocular pressures within the normal range, there may be benefits to prophylactically treat patients to maintain or further reduce their intraocular pressures, or reduce intraocular pressure fluctuation, to delay or prevent damage to the optic nerve. Individuals at risk of developing glaucoma include some racial groups (i.e. those of African or African American decent or Latina/Hispanic decent), individuals with a family history of glaucoma, thinness of the cornea, and abnormal optic nerve anatomy.

In accordance with one embodiment patients at risk of developing glaucoma are administered a composition comprising an inhibitor of orexin activity in an amount effective to reduce their intraocular pressure or fluctuations in their intraocular pressure over time. Any reduction in intraocular pressure resulting from the administration of the inhibitor of orexin activity is believed to be beneficial. In one embodiment the inhibitor of orexin activity is administered in an amount to reduce intraocular pressures to less than 21 mm Hg, 20 mm Hg, 19 mm Hg, 18 mm Hg, 17 mm Hg, 16 mm Hg, 15 mm Hg, 14 mm Hg, 13 mm Hg, or 12 mm Hg. In one embodiment a composition comprising an inhibitor of orexin activity is administered to reduce the patient's IOP by 20%, 15%, 10%, or 5%. In another embodiment the inhibitor of orexin activity is administered in an amount to reduce changes in pressure (i.e. the IOP fluctuation), measured by one skilled in the art of determining intraocular pressure, over the time period of hours, days, weeks, months or years. In accordance with one embodiment a composition comprising an inhibitor of orexin activity is administered to maintain fluctuation of IOP to within 20%, 15%, 10%, or 5% of the patient's average measured IOP as measured over the time period of hours, days, weeks, months or years. In one embodiment a composition comprising an inhibitor of orexin activity is administered to maintain fluctuation of IOP to within 10% of the patient's average measured IOP as measured over a time period of hours, days, weeks, months or years. In one embodiment, patients administered a composition comprising an inhibitor of orexin activity will experience a reduction of IOP and decreased fluctuations in IOP as measured over the time period of hours, days, weeks, months or years.

In one embodiment the composition comprising the inhibitor of orexin activity is administered by injection. In a further embodiment the composition comprises an orexin inhibitor selected from the group consisting of SB334867, MK4305 and Almorexant. In one embodiment the composition comprises the orexin inhibitor SB334867 administered at a dosage of about 24 mg/kg to about 36 mg/kg.

In accordance with one embodiment a method is provided for treating glaucoma. In one embodiment the method comprises the step of administering to a patient suffering from an undesirable intraocular pressure (IOP) or an undesirable fluctuation in the IOP, a composition comprising an inhibitor of orexin activity. The composition can be administered prophylactically (e.g., based on family history or detected physical changes associated with glaucoma) or can be administered at the onset of the excessive IOP or excessive IOP fluctuation.

Reducing orexin activity can be accomplished by interfering with the expression of orexin A and/or orexin B through standard techniques known to those skilled in the art including for example the use of a short hairpin RNA (shRNA), microRNA, antisense molecule, a small double stranded interference RNA (siRNA) directed to at least one of the genes that codes for orexin. Alternatively, the activity of orexins can be reduced by an antibody or other molecule that binds to orexin A and/or orexin B or their receptors, or otherwise interferes with the interaction of orexin A and/or orexin B with one or more of the ORX 1 or 2 receptors. As used herein the term "inhibitor of orexin activity" is intended to encompass any safe and effective compound or treatment that can be administered to a patient to inhibit orexin activity in vivo.

In accordance with one embodiment the inhibitor of orexin activity is an ORX 1 or 2 receptor antagonist. Preferably the compound is one that can penetrate the blood brain barrier. Orexin receptor antagonists having these properties are known to those skilled in the art and include, for example, inhibitors SB334867 (1-(2-methylbenzoxazol-6-yl)-3-[1,5] naphthyridin-4-yl urea):

MK4305 (a proprietary compound of Merck currently in Phase III testing) and Almorexant (2R)-2-[(1S)-6,7- dimethoxy-1-{2-[4-(trifluoromethyl)phenyl]ethyl}-3,4-di-hydroisoquinolin-2(1H)-yl]-N-methyl-2-phenylacetamide):

SB334867 is a drug which was the first non-peptide antagonist developed that is selective for the orexin receptor subtype ORX1, with around 100× selectivity for ORX1 over ORX2 receptors. Both MK4305 and Almorexant are competitive, dual $ORX_1$ and $ORX_2$ receptor antagonists and selectively inhibit the functional consequences of $ORX_1$ and $ORX_2$ receptor activation. In accordance with one embodiment one or more of these inhibitors are administered to a patient suffering from glaucoma and/or an undesirable intraocular pressure (IOP) in an amount sufficient to maintain low or baseline intraocular pressure (IOP), reduce intraocular pressure (IOP) or reduce or prevent an undesirable fluctuation in intraocular pressure (IOP). In one embodiment the patient is administered a composition comprising the orexin inhibitor in a standard pharmaceutically acceptable carrier using any of the standard routes of administration known those skilled in the art. In one embodiment the composition is administered by injection, and more particularly, by intravenous injection.

In one embodiment a kit is provided for administering the orexin inhibitor to a patient. The kit comprises one or more orexin inhibitors and instructional materials. In one embodiment the kit is provided with a device for administering an orexin inhibitor composition to a patient, e.g. syringe needle, pen device, jet injector or other needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the orexin inhibitor in a lyophilized form or in an aqueous solution. In another embodiment the orexin inhibitor is provided in a solid dosage form. Preferably, the kits will also include instructions for use. In one embodiment the orexin inhibitor is selected from the group consisting of SB334867, MK4305 and Almorexant and the device for administering the inhibitor is a syringe.

In accordance with one embodiment a method of reducing IOP or IOP fluctuation is provided wherein the patient is administered a composition that decreases overall orexin receptor activity (i.e., activity produced by both the ORX1 and ORX2 receptors). In another embodiment the method comprises administering a composition that selectively decreases orexin receptor activity of the ORX1 or ORX2 receptor. In accordance with one embodiment the method comprises administering an orexin inhibitory compound that is a selective orexin receptor subtype ORX1 antagonist or is selective for the orexin receptor subtype ORX2. In a further embodiment the patient is administered a composition comprising a dual ORX1 and ORX2 receptor antagonist. In one embodiment the patient is administered a selective inhibitor of orexin A activity. In an alternative embodiment the patient is administered a selective inhibitor of orexin B activity.

In one embodiment a method of treating a patient suffering from a) glaucomatous optic nerve damage;
b) visual field defects associated with glaucomatous optic nerve damage;
c) an increase in intraocular pressure;
d) intraocular pressure fluctuations or
e) any combination of a) through e) is administered a composition comprising an inhibitor of orexin activity. In one embodiment the composition comprises an orexin receptor antagonist selected from the group consisting of SB334867, MK4305 and Almorexant.

In one embodiment the inhibitor of orexin activity comprises an orexin receptor antagonist, including one or more of the compounds SB334867, MK4305 and Almorexant. In one embodiment the inhibitor is SB334867. The compounds are typically administered by intravenous injection at a dosage of about 20 mg/kg to about 50 mg/kg, more typically at about 24 mg/kg to about 36 mg/kg. In one embodiment the orexin receptor antagonist is administered at a dosage of about 27 mg/kg to about 33 mg/kg or at a dosage of about 30 mg/kg.

In exemplified embodiment 1 a method of lowering intraocular pressure or intraocular pressure fluctuations in a patient is provided, wherein the method comprises the step of administering to the patient a composition comprising an inhibitor of orexin activity. In one embodiment, in the method of exemplified embodiment 1 the composition is administered by injection, optionally with the composition comprising an ORX1 receptor antagonist and/or an ORX2 receptor antagonist. In one embodiment, in the method of exemplified embodiment 1 the composition comprises an orexin inhibitor selected from the group consisting of SB334867, MK4305 and Almorexant, and the composition is optionally administered orally.

In exemplified embodiment 2, a method of treating glaucoma is provided wherein the method comprises administering to a patient suffering from glaucomatous optic nerve damage and/or corresponding visual field defects, with or without an increase in intraocular pressure, a composition comprising an inhibitor of orexin activity. Optionally, said patient suffering from glaucomatous optic nerve damage and/ or corresponding visual field defects is experiencing intraocular pressure fluctuations which are diminished by the administration of a composition comprising an orexin inhibitor, said inhibitor optionally selected from the group consisting of SB334867, MK4305 and Almorexant, further wherein the composition is optionally administered orally. In one embodiment, in the method of exemplified embodiment 2 the composition is administered by injection or orally, optionally with the composition comprising an ORX1 receptor antagonist and/or an ORX2 receptor antagonist. In one embodiment, in the method of exemplified embodiment 2 the composition comprises an orexin inhibitor selected from the group consisting of SB334867, MK4305 and Almorexant, and the composition is optionally administered orally.

EXAMPLES

Example 1

Figure 1A:
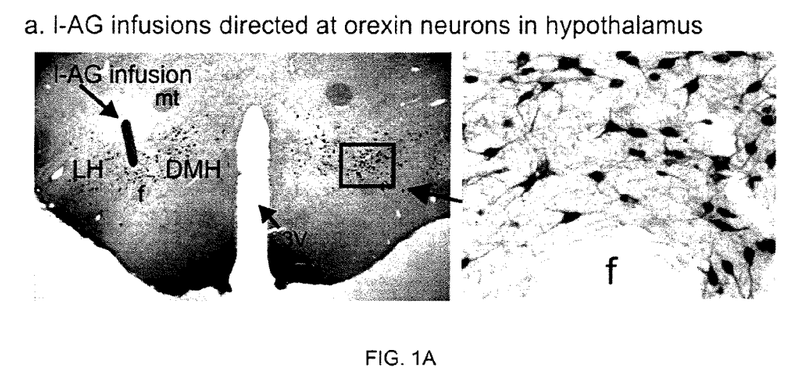
Figure 1B:
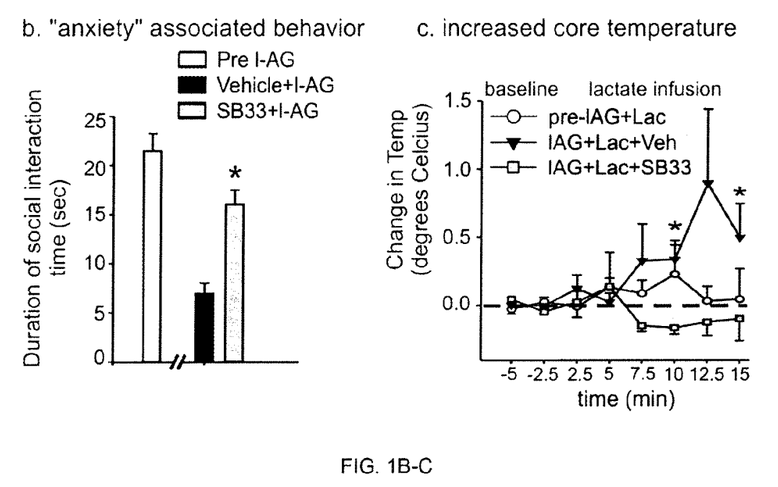
Figure 1D:
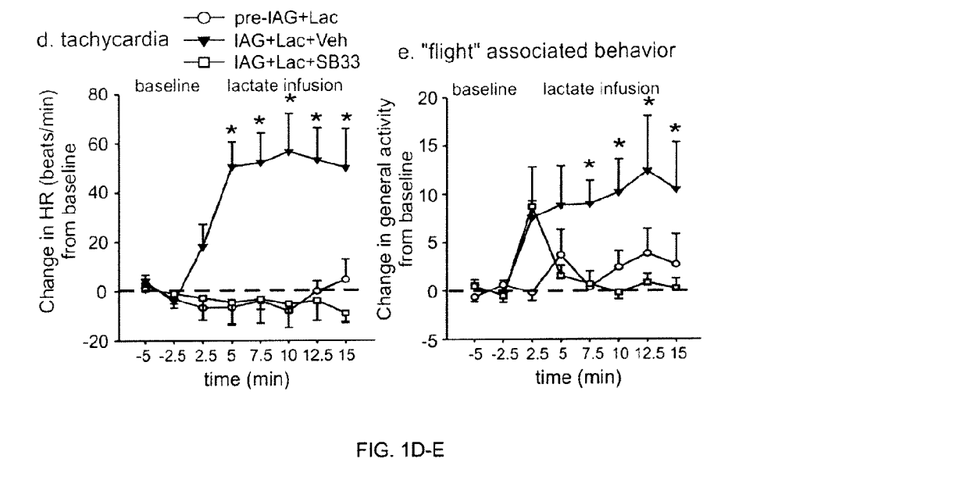

Administration of Orexin 1 Receptor Antagonist (SB334867) Blocks Sodium Lactate Induced Increases in Anxiety Panic disorder is associated with disruption of central inhibitory gamma-aminobutyric acid (GABAergic) tone, and may contribute to panic attacks which are consistently provoked by ordinarily mild physical stressors such as mild osmotic disturbances (e.g., intravenous sodium lactate challenges). Similarly, chronic disruption of GABAergic tone in the dorsomedial hypothalamus (a site that is critical for regulating adaptive panic/defense responses) of rats produces a vulnerability to panic-like anxiety and flight associated behavior and cardiorespiratory responses following intravenous 0.5 M sodium lactate, {Shekhar, 1997; Shekhar, 1996} {Shekhar, 2006} {Johnson, 2006; Johnson, 2007} providing an animal model of panic disorder. Orexin/hypocretin producing neurons are almost exclusive to dorsomedial hypothalamus/perifornical area and adjacent lateral hypothalamus, and play a critical role in maintaining wakefulness, vigilance and central sympathetic mobilization, which are key components of panic and anxiety. Experiments were conducted to investigate whether the administration of either a systemic orexin 1 antagonist or silencing the hypothalamic orexin gene product with RNA interference could block lactate-induced panic responses. The resulting data supports the hypotheses that panic-prone states in the animal model of panic are associated with selective activation of orexin-containing neurons. Furthermore, either systemic orexin 1 antagonists or silencing the hypothalamic orexin gene product with RNA interference blocked lactate-induced panic responses. Graphs in FIGS. 1b-e demonstrate that systemically injecting panic-prone rats with an orexin 1 receptor antagonist blocks sodium lactate induced increases in anxiety (FIG. 1b) and flight behavior (FIG. 1e) as well as thermogenic (FIG. 1c) and cardioexcitatory (FIG. 1d) responses. Thus, the data provides supports that aberrations of the hypothalamic orexin system underlie vulnerability to panic and potentially menopausal symptom clusters (e.g., sleep disturbance, anxiety, and depression). Accordingly orexin antagonists should provide a novel approach to treating these symptoms/symptom clusters.

Example 2

Figure 2A:
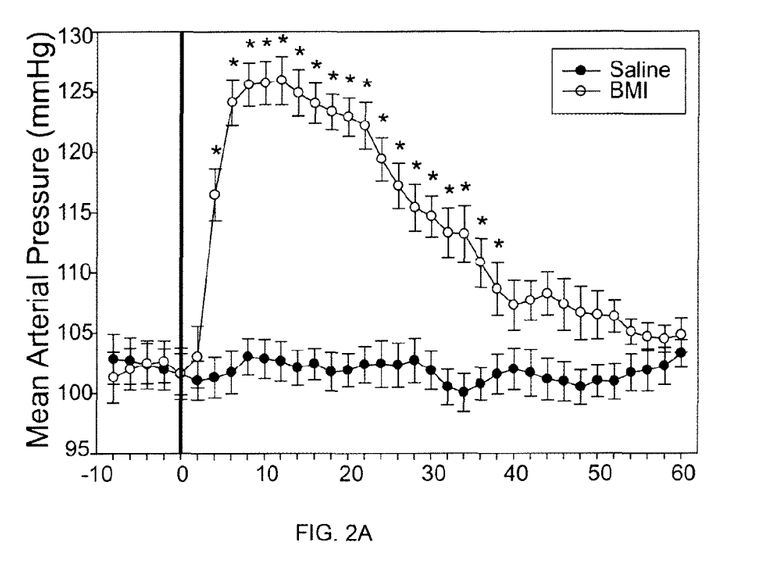
FIG. 2A-C Simultaneous measurement of blood pressure (FIG. 2A), heart rate (FIG. 2B), and IOP (FIG. 2C) in a series of isoflurane-anesthetized rats after infusion of bicuculline methiodide (30 pmol/75 nL; n=9) or saline vehicle (75 nL; n=10) into the region of the DMH. * indicates a significant difference ($p<0.05$) between the vehicle treated and the BMI treated group using a repeated measures ANOVA followed by post-hoc analysis for differences between timepoints using a t-test.
Figure 2B:
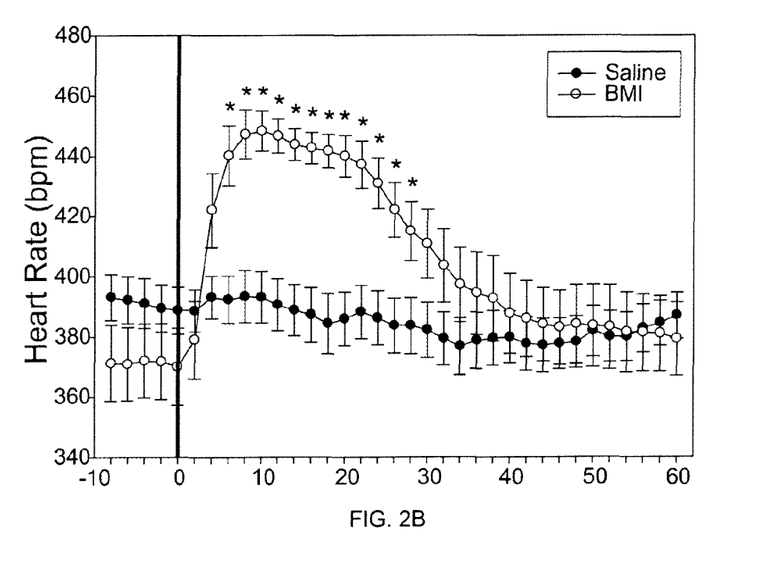
Figure 2C:
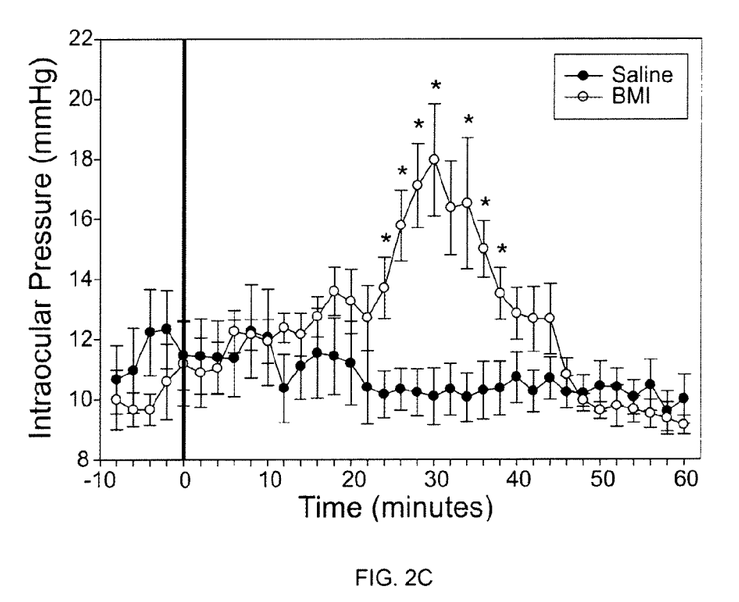

Role of Orexin Neurons in Regulating the Circadian Fluctuations in Intraocular Pressure To investigate whether orexin containing neurons located in the dorsomedial hypothalamus (DMH) and/or perifornical (PeF) area play a role in mediating the circadian fluctuations in IOP, isoflurane-anesthetized rats were administered orexin inhibitors and their vital functions were monitored. More particularly, simultaneous measurement of blood pressure (top panel), heart rate (middle panel), and intraocular pressure (bottom panel) in a series of isoflurane-anesthetized rats was measured after infusion of bicuculline methiodide (BMI; 30 pmol/75 nL; n=10 or saline vehicle (75 nL; n-9) into the region of the DMH. * indicates a significant difference ($p<0.05$) between the vehicle treated and the BMI treated group using a repeated measures ANOVA followed by post-hoc analysis for differences between timepoints using a t-test. As shown in FIG. 2, in addition to the expected increases in heart rate and blood pressure, chemical stimulation of the DMH also evoked an increase in IOP.

Figure 3:
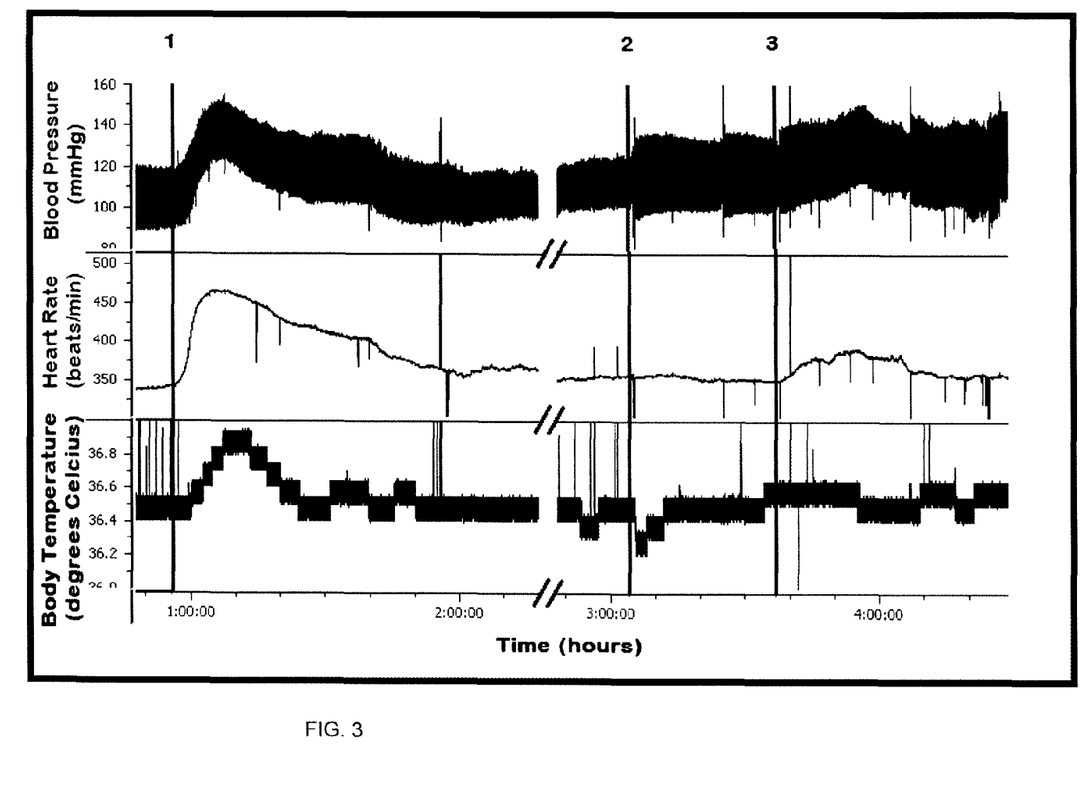
FIG. 3 Continuous and simultaneous measurement of blood pressure, heart rate, and core body temperature in an isoflurane anesthetized rat after identical microinjections of BMI (20 pmol/50 nL) into the DMH (time marks 1 and 3) before and after systemic administration of the orexin-1 receptor antagonist SB334861 (30 mg/kg i.p.; time mark 2). Note attenuation of all three measures after the administration of the orexin receptor antagonist.

Experiments were then conducted to determine whether an orexin-I receptor antagonist (SB334861) could attenuate the physiologic responses to chemical stimulation of the DMH. To test orexin inhibitors ability to attenuate the BMI stimulated response, BMI was administered to an isoflurane-anesthetized rat both before and after administration of the orexin inhibitor and the responses were monitored. The results are shown in FIG. 3 where continuous and simultaneous measurement of blood pressure (top panel), heart rate (middle panel), and core body temperature (bottom panel) were taken in an isoflurane anesthetized rat after identical microinjections of BMI (20 pmol/50 nL) into the DMH (time marks 1 and 3) before and after systemic administration of the orexin-1 receptor antagonist SB334861 (30 mg/kg i.p.; time mark 2). Note the significant attenuation of increased heart rate, blood pressure, and core body temperature that would normally occur after microinjection of BMI. This attenuation of all three measurements is the result of administration of the orexin receptor antagonist. It is anticipated that a similar attenuation of intraocular pressure will be obtained and the intraocular pressures can be lowered in animals receiving an inhibitor of orexin activity. Applicants believe orexin neurons mediate the circadian fluctuations in intraocular pressure that lead to the progression of glaucoma. With orexin neurons concentrated exclusively in the DMH, these neurons likely provide a novel target for future glaucoma therapies.

We claim:

1. A method of treating glaucoma in a patient in need thereof, the method comprising administering to the patient an effective amount of a composition comprising an inhibitor of orexin activity, the inhibitor being an orexin antagonist selected from the group consisting of 1-(2-methylbenzoxazol-6-yl)-3-[1,5]naphthyridin-4-yl urea (SB334867), [(7R)-4-(5-chloro-1,3-benzoxazol-2-yl)-7-methyl-1,4-diazepan-1-yl][5-methyl-2-(2H-1,2,3-triazol-2-yl)phenyl]methanone (MK4305), (2R)-2-[(1S)-6,7-dimethoxy-1-{2-[4-(trifluoromethyl)phenyl]ethyl}-3,4-dihydroisoquinolin-2(1H)-yl]-N-methyl-2-phenylacetamide (Almorexant), and combination thereof.

2. The method of claim 1 wherein the orexin antagonist is 1-(2-methylbenzoxazol-6-yl)-3-[1,5]naphthyridin-4-yl urea (SB334867).

3. The method of claim 1 wherein the orexin antagonist is administered at a dosage of about 24 mg/kg to about 36 mg/kg.

4. The method of claim 1 wherein the orexin antagonist is administered at a dosage of about 27 mg/kg to about 33 mg/kg.

5. The method of claim 1 wherein the patient in need is at risk of or suffering from at least one of glaucomatous optic nerve damage, a visual field defect and an elevated intraocular pressure.

6. The method of claim 5 wherein the administration of the inhibitor of orexin activity reduces intraocular pressure to about 10 mm Hg to about 21 mm Hg.

7. A method of reducing intraocular pressure in a patient in need thereof, the method comprising administering to the patient an effective amount of a composition comprising an inhibitor of orexin activity, the inhibitor being an orexin antagonist selected from the group consisting of 1-(2-methylbenzoxazol-6-yl)-3-[1,5]naphthyridin-4-yl urea (SB334867), [(7R)-4-(5-chloro-1,3-benzoxazol-2-yl)-7-methyl-1,4-diazepan-1-yl][5-methyl-2-(2H-1,2,3-triazol-2-yl)phenyl]methanone (MK4305), (2R)-2-[(1S)-6,7-dimethoxy-1-{2-[4-(trifluoromethyl)phenyl]ethyl}-3,4-dihydroisoquinolin-2(1H)-yl]-N-methyl-2-phenylacetamide (Almorexant), and combination thereof.

8. The method of claim 7 wherein the administration of the inhibitor of orexin activity reduces intraocular pressure to about 10 mm Hg to about 21 mm Hg.

9. The method of claim 7 wherein the orexin antagonist is 1-(2-methylbenzoxazol-6-yl)-3-[1,5]naphthyridin-4-yl urea (SB334867).

10. The method of claim 7 wherein the orexin antagonist is administered at a dosage of from about 24 mg/kg to about 36 mg/kg.

11. A method for maintaining intraocular pressure in a patient in need thereof, the method comprising administering to the patient an effective amount of a composition comprising an inhibitor of orexin activity, the inhibitor being an orexin antagonist selected from the group consisting of 1-(2-methylbenzoxazol-6-yl)-3-[1,5]naphthyridin-4-yl urea (SB334867), [(7R)-4-(5-chloro-1,3-benzoxazol-2-yl)-7-methyl-1,4-diazepan-1-yl][5-methyl-2-(2H-1,2,3-triazol-2-yl)phenyl]methanone (MK4305), (2R)-2-[(1S)-6,7-dimethoxy-1-{2-[4-(trifluoromethyl)phenyl]ethyl}-3,4-dihydroisoquinolin-2(1H)-yl]-N-methyl-2-phenylacetamide (Almorexant), and combination thereof.

12. The method of claim 11 wherein the administration of the inhibitor of orexin activity maintains intraocular pressure at a pressure of about 10 mm Hg to about 21 mm Hg.

\* \* \* \* \*